United States Patent [19]
Welcome

[11] Patent Number: 5,415,157
[45] Date of Patent: May 16, 1995

[54] DAMAGE PREVENTING ENDOSCOPE HEAD COVER

[76] Inventor: Steven Welcome, 18708 Flower Hill Way, Gaithersburg, Md. 20879

[21] Appl. No.: 13,868

[22] Filed: Feb. 5, 1993

[51] Int. Cl.$^6$ .............................................. A61B 1/00
[52] U.S. Cl. ...................................... 128/4; 206/571; 206/592; 206/587
[58] Field of Search ............... 206/571, 316.1, 446, 206/521, 522, 585, 587, 588, 591, 592, 594, 303, 305, 306, 363, 364, 370, 438; 128/4; 606/1; 604/263, 163; 134/201; 138/110

[56] References Cited

U.S. PATENT DOCUMENTS

| | | |
|---|---|---|
| 2,958,364 | 11/1960 | Thompson . |
| 3,473,646 | 10/1969 | Burke .................................. 206/571 X |
| 3,723,061 | 3/1973 | Stahl .................................. 206/592 X |
| 3,861,395 | 1/1975 | Taniguchi . |
| 3,983,996 | 10/1976 | Hendren, III ................... 206/587 X |
| 4,356,610 | 11/1982 | Hon et al. . |
| 4,646,722 | 3/1987 | Silverstein et al. . |
| 4,676,228 | 6/1987 | Krasner et al. . |
| 4,721,097 | 1/1988 | D'Amelio .............................. 128/4 |
| 4,731,505 | 3/1988 | Crenshaw et al. ............. 138/110 X |
| 4,754,877 | 7/1988 | Johansson et al. . |
| 4,772,275 | 9/1988 | Erlich . |
| 4,878,485 | 11/1989 | Adair . |
| 4,974,580 | 12/1990 | Anapliotis . |

FOREIGN PATENT DOCUMENTS

| | | |
|---|---|---|
| 0440252 | 8/1991 | European Pat. Off. . |
| 0440253 | 8/1991 | European Pat. Off. . |
| 0440254 | 8/1991 | European Pat. Off. . |
| 3508833 | 9/1986 | Germany .................. 128/4 |

*Primary Examiner*—Richard J. Apley
*Assistant Examiner*—Beverly A. Meindl

[57] ABSTRACT

A surgical endoscope head is protected against damage from impact during non-surgical handling and disinfecting procedures by inserting the head into a protective sleeve. The sleeve has sufficient rigidity to resist deformation from impact experienced during handling. The inserted head is spaced from the sleeve interior to permit free flow of disinfectant liquid about the head periphery. Additional protection may be provided by a sheath disposed concentrically within the sleeve and adapted to receive the protected endoscope head while providing for free flow of liquid around and along the head. The endoscope head is preferably gripped resiliently at the proximal end of the sleeve without blocking liquid flow through the open proximal end.

20 Claims, 2 Drawing Sheets

DAMAGE PREVENTING ENDOSCOPE HEAD COVER

BACKGROUND OF THE INVENTION

1. Technical Field

The present invention relates to methods and apparatus for protecting surgical endoscopes against damage during transport, handling and disinfection procedures.

2. Discussion of the Prior Art

The distal ends or heads of surgical endoscopes are typically somewhat bendable cylindrical members circumferentially bound by a fluid-impervious polymeric wrapping and containing electronic chips and other delicate components. It is not uncommon for the polymeric wrapping to be punctured or ripped when carelessly handled during storage or removal from storage or while being disinfected between surgical procedures. Specifically, the endoscope assembly is somewhat unwieldy to handle, and the distal end is often dropped onto a floor or other hard surface, sometimes being inadvertently kicked or stepped on. The unwieldiness of the assembly can also result in the distal end impacting against a table, cabinet or other fixture while the assembly is being handled or carried from one location to another. In addition to the potential for rupture and puncture of the polymeric wrapping, the impact of the head against a hard surface can cause damage to the interior components of the head, particularly sensitive optical components and integrated circuit chips of an endoscope camera. Puncture or rupture of the polymeric wrapping, if undetected, results in disinfectant liquid entering the endoscope head and damaging the components.

OBJECTS AND SUMMARY OF THE INVENTION

It is an object of the present invention to provide a method and apparatus for preventing damage to the head of a surgical endoscope when the endoscope is not being used in a surgical procedure.

It is another object of the present invention to protect the sensitive distal end of a surgical endoscope against impact and rupture resulting from mishandling of the endoscope assembly during handling, transport and disinfection.

In accordance with the present invention, a shock absorbing sleeve is selectively engageable about the distal end of a surgical endoscope to protect the endoscope head from damage due to inadvertent impact of the head during mishandling of the endoscope. The sleeve is provided with drain openings to permit the endoscope head to be immersed in disinfectant liquids with the sleeve in place. The semi-rigid but resilient sleeve has a resilient and inwardly projecting gripping member of generally oval transverse cross-section at its proximal end with a minor axis dimension smaller than the diameter of the protected distal end of the endoscope. The major axis dimension of the oval gripping member is significantly larger than the endoscope head diameter. Accordingly, by diametrically squeezing and compressing the proximal end of the sleeve along its major cross-section axis, the minor axis dimension of the gripping member is temporarily enlarged to permit the endoscope to be inserted into and removed from the sleeve. When the diametric compressive force on the sleeve is released, the gripping member returns toward its normal configuration wherein the endoscope head is firmly and resiliently gripped at the proximal end of the sleeve between opposing walls along the minor cross-section dimension of the gripping member.

In one embodiment of the invention the protective cover includes an inner sheath disposed concentrically within the outer sleeve, and secured to the sleeve only at the proximal ends of the sleeve and sheath but spaced elsewhere along the sleeve and sheath lengths to provide greater shock absorbency. The protected endoscope head is inserted into the inner sheath and is preferably centered by means of ribs or protrusions extending inwardly from the sheath wall to minimize contact between the sheath and the endoscope head. Shock absorbing ribs may also be disposed between the sheath and sleeve. The sheath is provided with openings along its length to permit free flow of disinfectant liquid between the sheath interior and exterior during disinfection procedures. Both the sheath and the outer sleeve have openings at their proximal and distal ends to permit the disinfectant liquid to freely drain from the assembly.

The above and still further objects, features and advantages of the present invention will become apparent upon consideration of the following detailed description of a specific embodiment thereof, particularly when taken in conjunction with the accompanying drawings wherein like reference numerals in the various figures are utilized to designate like components.

DESCRIPTION OF THE PREFERRED EMBODIMENTS

Figure 1:
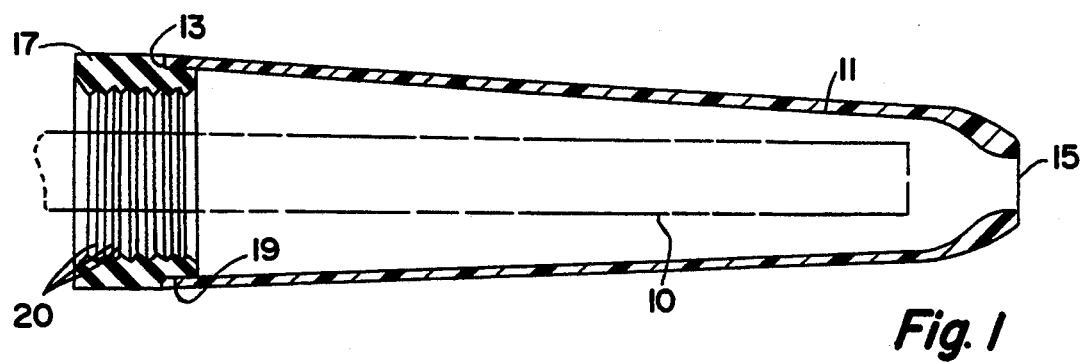
FIG. 1 is a view in longitudinal section of a first embodiment of the protective cover of the present invention, and illustrates a protected endoscope head in dashed lines.
Figure 2:
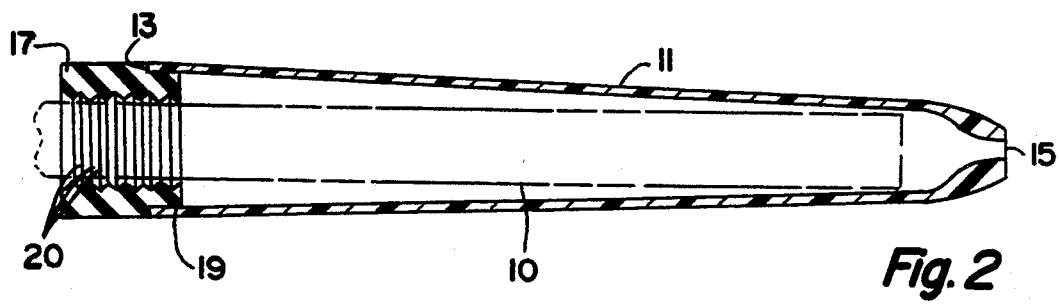
FIG. 2 is a view in longitudinal section of the embodiment illustrated in FIG. 1 with the cover rotated ninety degrees about its longitudinal axis.

Referring specifically to FIGS. 1 and 2 of the accompanying drawings, the distal end or head 10 of a surgical endoscope is shown in dashed lines inserted into a protective sleeve 11. Endoscope head 10 is conventional and typically contains, inter alia, a CCD camera chip and/or optical elements that can be damaged by severe impact and/or direct exposure to liquid. For this reason, the endoscope head is conventionally wrapped circumferentially with pliable polymeric material permitting the head to be flexed in use while providing some degree of protection against impact and a seal against liquid exposure. However, in practice, it is found that endoscopes are often mishandled to the point where the protective wrapping is punctured or ripped. Moreover, the wrapping provides only minimal protection for the interior components against damage resulting from impact if the endoscope head is dropped or collides with a hard object.

Protective sleeve 11 is an elongated hollow member having a generally oval transverse cross-section that becomes gradually smaller from its proximal open end 13 toward its distal open end 15. Sleeve 11 is made from a plastic sufficiently rigid to resist deformation in response to sharp impact against a hard edge or surface. In this manner, the retained endoscope head 10 is protected from damage due to impact. The sleeve material may also be sufficiently resilient, at least at the proximal end 13 of the sleeve, to permit manually induced deformation when inserting and removing the endoscope head in the manner described below. The axial length of sleeve 11 is sufficient to permit the sensitive length portion of endoscope head 10 to be fully inserted into the sleeve with the distal end of head 10 displaced proximally from the open distal end 15 of the sleeve.

Both the major and minor width dimensions of the oval transverse cross section of sleeve 11 become gradually smaller toward distal sleeve end 15, starting with widths at proximal end 13 that are larger than the diameter of endoscope head 10, and tapering to widths at distal end 15 that may be smaller than the endoscope head diameter. The maximum major width dimension (as seen in FIG. 1) at proximal end 13 is approximately three times the diameter of head 10. The minor width dimension (as seen in FIG. 2) at proximal end 13 is less than twice the scope head diameter.

A resilient elastomeric gripping member 17, made of rubber or similar material, is secured to the proximal end 13 of sleeve 11. Gripping member 17 is a short cylindrical section with an oval transverse cross section and has an outside surface preferably matching the oval outside configuration of sleeve 11 at proximal end 13. In this manner, the outside surface of gripping member 17, when engaged at proximal end 13, forms a uninterrupted longitudinal extension of the sleeve. Engagement between gripping member 17 and sleeve 11 is provided by reducing the outside diameter of an axially short distal section 19 of the gripping member. The reduced diameter distal end of the gripping member is then inserted in a forced fit relation into the proximal end 13 of sleeve 11. The depth of the reduced diameter section preferably matches the thickness of sleeve 11 to assure a continuous profile of the assembled components. Suitable adhesive may be used between the abutting surfaces of sleeve 11 and gripping member 17 to ensure that they do not become disengaged.

The interior surface of gripping member 17 is provided with a series of longitudinally sequential gripping ribs 20 facing inwardly of the member. Gripping ribs 20 may be disposed continuously along the entire interior surface of the gripping member, as shown; alternatively, the gripping ribs may be disposed only along a portion of the two more closely spaced and longer sides of the oval member. In either case, when the gripping member is in its natural or unflexed state, gripping ribs 20 on the longer interior sides (i.e., facing along the minor diameter of the oval) are spaced by a distance sufficiently smaller than the diameter of endoscope head 10 to cause the head to be positively gripped by the facing ribs. Endoscope head 10 can be inserted into or removed from sleeve 11 by compressing the shorter opposed ends of gripping member 17 toward one another along the major diameter of the oval, thereby causing the longer gripping sides to spread apart along the minor dimension and permit passage of head 10 therethrough.

As an alternative to a separate gripping member, the proximal end of sleeve 11 can be provided with an inwardly turned end portion having a resilient oval configuration suitable for serving the gripping function. As a further alternative, a separate clamp or clip can be attached to the outside of sleeve 11 and arranged to be selectively attachable to an exposed part of head 10 extending out from proximal sleeve end 13. Whatever arrangement is used to engage head 10, the head extends into sleeve 11 to a location close to but proximally spaced from distal end 15 of sleeve 11 so that the entire vulnerable length portion of the head is disposed in and protected by the sleeve.

The tapering cross section of sleeve 11 and its open ends 13 and 15 permit free flow of disinfectant solution about the inserted head 10 when the sleeve and the engaged head are disposed in a disinfectant bath. Endoscope head 10 may thus be protected against impact damage during a disinfecting procedure as well as during transportation, storage, and handling while awaiting use in a surgical operating room environment. The taper in the cross section of sleeve 11 is preferably such that the distal end of endoscope head 10, when fully inserted into the sleeve, does not contact the sleeve interior. However, contact with the sleeve about the very tip of head 10 is permissible and within the scope of the invention.

Figure 3:
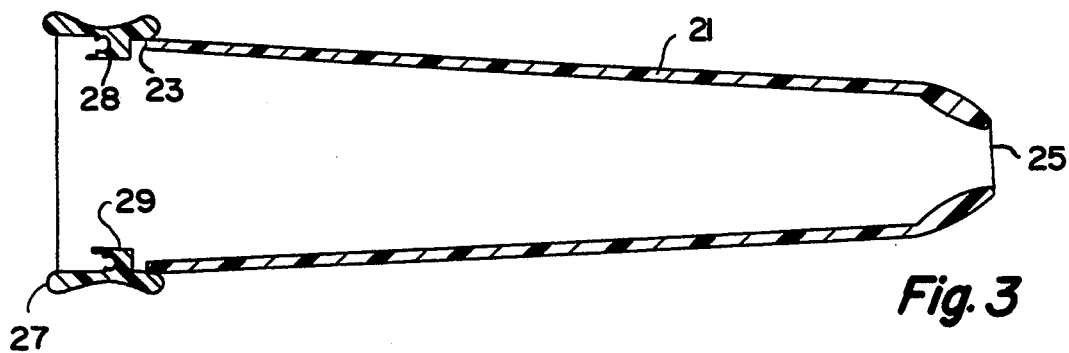
FIG. 3 is a view in longitudinal section of an outer sleeve constituting one part of a two-part second embodiment of the protective cover of the present invention.
Figure 4:
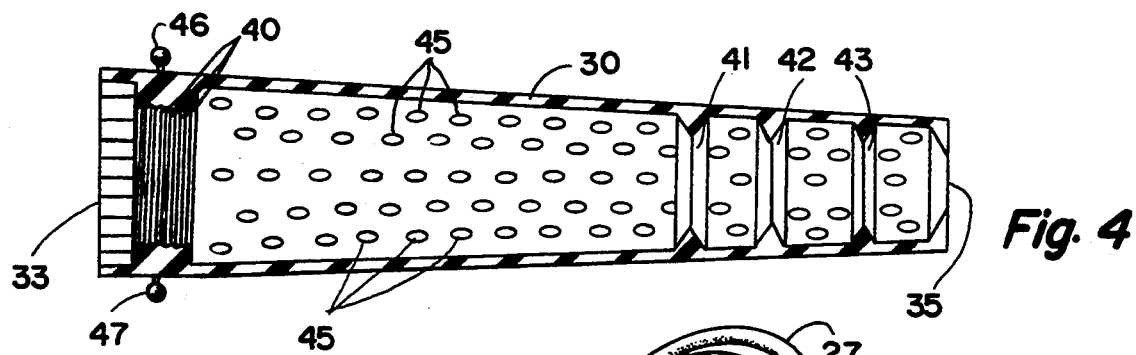
FIG. 4 is a view in longitudinal section of an inner sheath constituting the second part of the second embodiment of the present invention.
Figure 5:
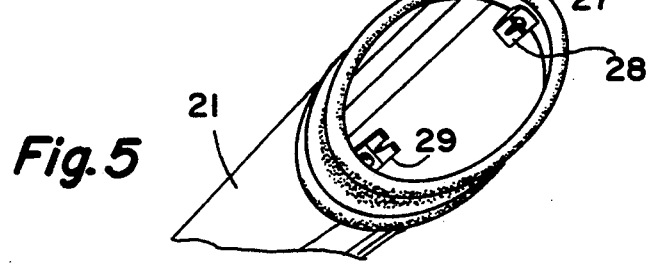
FIG. 5 is a view in perspective of the proximal end of the outer sleeve of FIG. 3.

Referring to FIGS. 3, 4 and 5, another embodiment of the endoscope head protective cover takes the form of an outer sleeve 21 and inner sheath 30 secured coaxially therein. Both sleeve 21 and sheath 30 are elongated hollow members having generally oval transverse cross sections. These sections gradually taper in a distal direction. Sleeve 21 is generally similar to sleeve 11 (FIGS. 1 and 2) described above and takes the form of a solid imperforate member having open proximal and distal ends 23 and 25, respectively. The plastic material employed for sleeve 21 is sufficiently rigid to resist deformation in response to impact against a hard surface. If no separate gripping member is utilized with sleeve 21, the sleeve must also be sufficiently resilient, at least at its proximal end, to permit deformation of the proximal end as necessary to insert, remove and grip an endoscope head.

In the embodiment illustrated in FIGS. 3, 4 and 5, an elastomeric gripping member 27 is secured by adhesive, or the like, to proximal end 23 of sleeve 21. Gripping member 27 is a short cylindrical member having a generally oval transverse cross section. The exterior surface of gripping member 27 is preferably contoured, at least at its opposite shorter ends (i.e., along the major oval dimension), to efficiently accommodate a person's thumb and index finger for the purpose of squeezing those ends together. The interior surface of gripping member 27 is substantially smooth except for two inwardly projecting receivers 28 and 29 also located at the opposite shorter ends. Receivers 28 and 29 each take the form of an L-bracket with a first leg projecting laterally inward from the interior surface of gripping member 27, and a second leg extending longitudinally in a proximal direction along the sleeve from the distal end of the first leg. A longitudinal slot is defined through the second leg from the distal end of the leg to a location spaced from the first leg. The interior space between the two legs of each receiver 28, 29 is contoured to have a partially spherical configuration opening in a proximal direction.

Interior sheath 30 is configured to be retained within sleeve 21 in spaced relation to the interior surface of the sleeve. Accordingly, the oval transverse cross section of sheath 30 is smaller than that of sleeve 21 at all corresponding points along the lengths of these elements. In addition, sheath 30 is sufficiently shorter than sleeve 21 to permit its open distal end 35 to terminate within sleeve 21, without contacting the sleeve, when the sheath is fully inserted into the sleeve. Near the proximal open end 33 of sheath 30 there are longitudinally sequential gripping ribs 40 defined along the entire interior surface; alternatively, these gripping ribs need only be formed along the more closely spaced opposite longer sides of the interior surface. Gripping ribs 40 project inwardly, at least along the minor diameter of the oval, to define a distance between the long sides, when unflexed, that is smaller than the diameter of the protected endoscope head.

Sheath 30 is made of a plastic material that need not but may be rigid to resist deformation on impact as required of the outer sleeve 21. Rather, sheath 30 may be made of elastomeric material and must be sufficiently compressible and resilient at its proximal end 33 to permit deformation of the opening between gripping ribs 40. One or more additional gripping ribs 41, 42, 43 project inwardly from respective longitudinal locations along sheath 30 intermediate ends 33 and 35. Ribs 41, 42, 43 are sized to resiliently engage the protected endoscope head when it is forced axially through the rib centers. Note that it is only the rib portions along the long sides of the sheath cross section that engage the endoscope head, and that there is space between the endoscope head and the shorter, more distantly spaced ends of the ribs (i.e., along the major diameter of the sheath cross section). Accordingly, disinfectant liquid is free to flow uninterruptedly in sheath 30 throughout the entire sheath length. Ribs 41, 42, 43 thus cooperate with ribs 40 to hold the endoscope head in place while permitting free fluid flow around the head. To further facilitate flow of disinfectant liquid along the protected endoscope head, multiple holes or apertures 45 are defined through sheath 30 at various locations.

In order to secure sheath 30 within sleeve 21, spherical supports 46, 47 extend radially outwardly from the sheath at a longitudinal location corresponding to the location of ribs 40. Supports 46 and 47 are disposed centrally of the long ends of the sheath cross section in positions corresponding to those of receivers 28 and 29, respectively, on gripping member 27. The spherical supports are disposed at the ends of short radially extending posts configured to be slidable through the slots in receivers 28, 29 to permit the spherical supports 46, 47 to be pushed into the partially spherical space defined in the receivers. The configurations of the spherical supports and partially spherical receivers are such that the supports are engageable in a snap fit relation within the receivers. When thusly supported, sheath 31 is spaced inwardly from sleeve 21 along the entire sheath length. The spacing provides two desirable features. First, disinfectant liquid is free to flow into sheath 30 from the interior of sleeve 21 through holes 45 without being blocked by any flush contact between surfaces of the sheath and sleeve. Second, the spacing between the sheath and sleeve provides an extra measure of shock absorbency for the protected endoscope head. More specifically, in this embodiment the endoscope head is protected not only by the rigidity of sleeve 21, but also by the cushion of air disposed between the sheath and sleeve.

Figure 7:
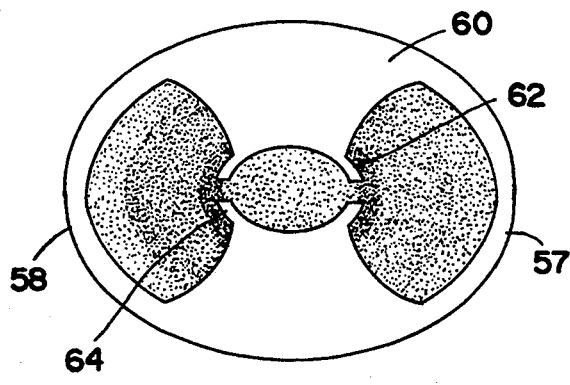
FIG. 7 is a proximal end view in plan of the embodiment of FIG. 6.
Figure 6:
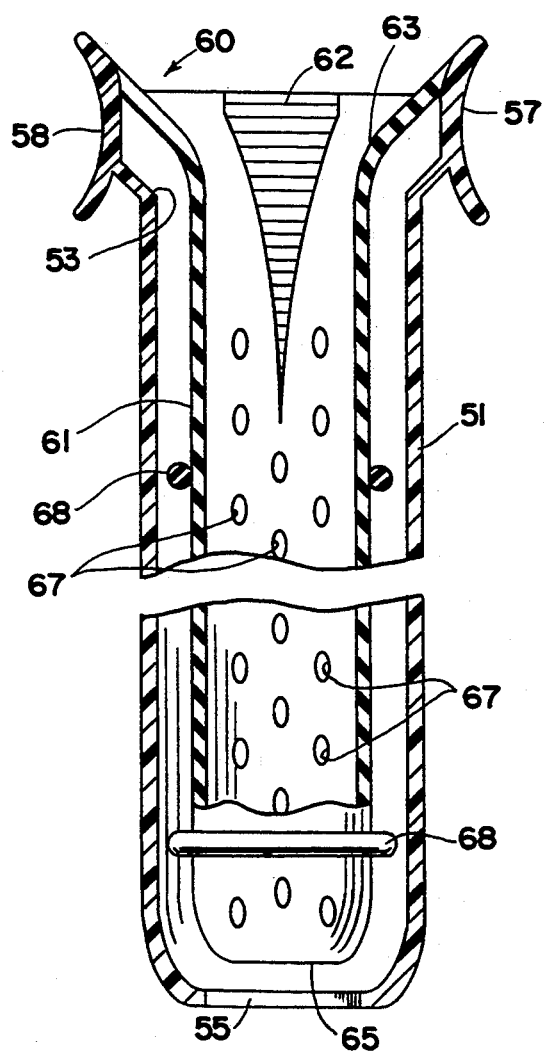
FIG. 6 is a view in longitudinal section of a third embodiment of the protective cover of the present invention.

The embodiment illustrated in FIGS. 6 and 7 includes an outer sleeve 51 and inner sheath 61 constructed as a single unit. In this embodiment sleeve 51 and sheath 61 have oval cross sections but do not necessarily taper toward their distal ends. Specifically, outer sleeve 51 is a rigid plastic member having an open distal end 55. Sheath 61 may be a less rigid plastic member with smaller cross sectional dimensions and having an open distal end 65 and multiple apertures 67 defined through the sheath along its length. Proximal end 53 of sleeve 51 and proximal end 63 of sheath 61 are joined (e.g., by ultrasonic welding, adhesive, or the like) at a resilient termination region 60. Opposed finger grips 57 and 58 are positioned at regions 60 on the outside surface of the arcuately shorter ends of sleeve 51 (i.e., at opposite ends of the major diameter of the oval cross section). Sheath 61 joins finger grips 57, 58 at their proximal ends; sleeve 51 joins the finger grips at a location intermediate the proximal and distal ends of the finger grips.

A pair of resilient head gripping members 62, 64 project radially inward from the longer oval sides (i.e., along the minor diameter of the oval) at the proximal end of sheath 61 in region 60. The mutually facing surfaces of gripping members 62, 64 are configured arcuately with a radius of curvature equal to or slightly smaller than the radius of the endoscope head to be protected. In addition, in the natural or unflexed position of region 60, members 62, 64 are spaced along the oval minor dimension by a distance that is shorter than the endoscope head diameter. Accordingly, to insert the endoscope head into the proximal end of the unit, region 60 is compressed along the major dimension of oval region 60 by squeezing inwardly on the finger grips 57, 58. As a consequence, the spacing between gripping members 62, 64 increases to permit the endoscope head to be inserted longitudinally between these members. When the endoscope head is inserted to the desired depth, the compressive force on finger grips 57, 58 is released, thereby permitting gripping members 62 and 64 to move toward one another and resiliently engage the endoscope head therebetween. The arcuate and resilient gripping members conform to the periphery of the engaged endoscope head, particularly if, as preferred, the radius of curvature of the members 62, 64 is somewhat smaller than the radius of the engaged head.

One or more shock absorbing elastomeric bumpers 68 may be disposed about sheath 61 at various longitudinally spaced locations. Bumpers 68 may be secured to or merely slidable along the sheath and serve to cushion impact between the sheath and the interior wall of sleeve 51. Such impact might occur, for example, if the endoscope head and cover are dropped and sleeve 51 falls onto a hard floor. The momentum of the distal end of sheath 61 tends to respond to this by impacting against the sleeve. However, bumpers 68 cushion that impact to provide further protection for the inserted endoscope head. It will be appreciated that similar bumpers may be provided about sheath 30 (FIG. 4) to serve the same protective function. In addition, bumpers may be provided on the interior surface of sleeve 11 (FIG. 1) to directly cushion the inserted endoscope head against impacting the interior sleeve wall.

Figure 8:
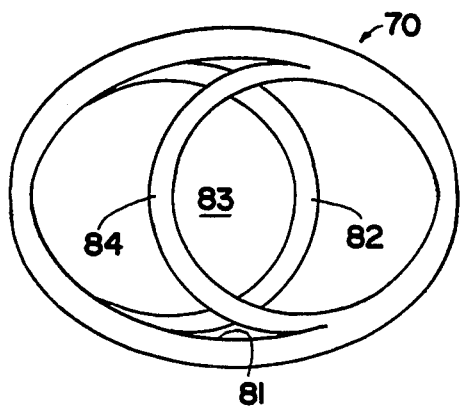
FIG. 8 is a proximal end view of a fourth embodiment of the protective cover of the present invention.

The gripping members 62, 64 illustrated in FIG. 7 have a particularly advantageous configuration in that they conform to the engaged endoscope head. However, that particular configuration is not limiting on the scope of the present invention. An alternative gripping member configuration is illustrated in FIG. 8 wherein the gripping region 70, of a device otherwise constructed similar to that of FIG. 6, includes two generally oval gripping rings 82, 84 secured to, and preferably integrally formed with, the shorter sides of sheath 81. Oval gripping rings 82, 84 are smaller than the oval periphery of the gripping region 70 and have their major diameters disposed colinearly with the major diameter of region 70. Gripping rings 82, 84 are resilient and have a sufficiently long major diameter to overlap and define a space 83 between their overlapping portions. The overlap space 83, along the major diameters of rings 82, 84, is shorter than the diameter of the endoscope head that is to be protected. Accordingly, region 70 must be compressed along its major diameter to increase the length of space 83 along that diameter, and to permit insertion and withdrawal of the endoscope head. When the compression forces are removed, the endoscope head is positively engaged within space 83 by gripping rings 82 and 84. The remainder of the unit illustrated in FIG. 8 may be substantially similar to the unit illustrated in FIG. 6.

The present invention provides a method and apparatus for protecting the sensitive and vulnerable head of an endoscope from damage due to impact during handling while permitting free flow of disinfectant liquid about the exterior surface of the protected head.

Having described preferred embodiments of my invention, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A protective cover for protecting a surgical endoscope head when not in use comprising:
   an elongated protective sleeve having a hollow interior, an open proximal end and an open distal end;
   at least one gripping device for selectively positionally securing the endoscope head relative to said sleeve with said endoscope head inserted within said hollow interior of said sleeve through said proximal end and recessed from said distal end; and
   a flow passage for freely conducting disinfectant fluid in contact with said endoscope head when inserted into said sleeve and gripped by said gripping device;
   wherein said sleeve is sufficiently rigid to retain its elongated shape without additional support and to resist deformation and bending.

2. The protective cover of claim 1 wherein said gripping device includes first and second opposed gripping members extending generally radially inward of said sleeve to define a gripping space therebetween at a location adjacent said proximal end, said gripping device being more resilient than said sleeve to permit selective enlargement of said gripping space, wherein said gripping members have an unstressed position in which the distance between the gripping members is shorter than the thickness of said endoscope head.

3. The protective cover of claim 2 wherein said gripping device is a generally cylindrical elastomeric member secured coaxially to the end of said sleeve, and wherein each of said gripping members includes a plurality of longitudinally sequential gripping ribs extending radially inward from said opposite sides of said device.

4. A protective cover for a surgical endoscope head comprising:
   an elongated protective sleeve having a hollow interior, an open proximal end and a distal end;
   at least one gripping device for selectively positionally securing the endoscope head relative to said sleeve with said endoscope head inserted within said hollow interior of said sleeve through the proximal end; and
   a flow passage for freely conducting fluid along said endoscope head when inserted into said sleeve and gripped by said gripping device;
   wherein said sleeve is sufficiently rigid to retain its elongated shape without additional support and to resist deformation and bending upon impact against a hard surface;
   wherein said gripping device includes first and second opposed gripping members extending generally radially inward of said sleeve to define a gripping space therebetween at a location adjacent said proximal end, said gripping device being more resilient than said sleeve to permit selective enlargement of said gripping space, wherein said gripping members have an unstressed position in which the distance between the gripping members is shorter than the thickness of said endoscope head;
   wherein said gripping device is a generally cylindrical elastomeric member secured coaxially to the end of said sleeve, and wherein each of said gripping members includes a plurality of longitudinally sequential gripping ribs extending radially inward from said opposite sides of said device;
   wherein said sleeve has a generally oval transverse cross section tapering in size from said proximal end to said distal end, and wherein said gripping device has an interior surface defining an oval with a minor diameter smaller than the diameter of the protected endoscope head.

5. A protective cover for a surgical endoscope head comprising:
   an elongated protective sleeve having a hollow interior, an open proximal end and a distal end;
   at least one gripping device for selectively positionally securing the endoscope head relative to said sleeve with said endoscope head inserted within said hollow interior of said sleeve through the proximal end; and
   a flow passage for freely conducting fluid along said endoscope head when inserted into said sleeve and gripped by said gripping device;
   wherein said sleeve is sufficiently rigid to retain its elongated shape without additional support and to resist deformation and bending upon impact against a hard surface; and
   an inner sheath disposed within said sleeve for receiving the endoscope head, said inner sheath having a distal end and a proximal end secured to said sleeve, and an elongated hollow body extending longitudinally in said sleeve and in spaced relation relative to said sleeve, wherein said distal end of said sheath is disposed within said sleeve proximally of the distal end of said sleeve.

6. The protective cover of claim 5 wherein said sheath has multiple openings defined therein to permit liquid to flow freely into and out of said sheath.

7. The protective cover of claim 6 wherein both said distal end of said sheath and said distal end of said sleeve are open.

8. The protective cover of claim 7 wherein said sheath is selectively removable from and insertable into said sleeve.

9. The protective cover of claim 8 wherein said gripping device is secured to the proximal end of said sheath and has an interior surface defining an oval with a minor diameter smaller than the diameter of the protected endoscope head, and wherein the gripping device is selectively compressible along a major diameter of said oval to effect selective expansion of said minor diameter and thereby permit insertion and removal of the endoscope head.

10. The protective cover of claim 7 further comprising at least one shock absorber disposed on said sheath to cushion impact between said sheath and said sleeve.

11. In combination:
 a surgical endoscope having a head with a generally cylindrical periphery and containing impact-vulnerable components;
 an elongated protective sleeve having a hollow interior with a transverse cross section larger than said endoscope head, an open proximal end and a distal end;
 at least one gripping device for selectively positionally securing said endoscope head within said sleeve with said endoscope head extending into said hollow interior of said sleeve through said proximal end; and
 a flow passage for freely conducting disinfectant liquid in said sleeve in contact with the periphery of said endoscope head;
 wherein said sleeve is sufficiently rigid to retain its elongated shape without additional support and to resist deformation and bending upon impact against a hard surface.

12. The protective cover of claim 11 wherein said gripping device includes first and second opposed gripping members extending generally radially inward of said sleeve to define a gripping space therebetween at a location adjacent said proximal end, said gripping device being more resilient than said sleeve to permit selective enlargement of said gripping space, wherein said gripping members have an unstressed position in which the distance between the gripping members is shorter than the thickness of said endoscope head.

13. The endoscope head of claim 12 wherein said gripping device is a generally cylindrical elastomeric member secured coaxially to the proximal end of said sleeve, and wherein each of said gripping members includes a plurality of longitudinally sequential gripping ribs extending radially inward from opposite sides of said member; and wherein said gripping device has an interior surface defining an oval with a minor diameter smaller than the diameter of the protected endoscope head.

14. The combination of claim 11 further comprising:
an inner sheath disposed within said sleeve for receiving the endoscope head, said inner sheath having a distal end and a proximal end secured to said sleeve, and an elongated hollow body extending longitudinally in, and in spaced relation relative to, said sleeve, wherein said distal end of said sheath is disposed within said sleeve proximally of the distal end of said sleeve.

15. The combination of claim 14 wherein said sheath has multiple openings defined therein to permit liquid to flow freely into and out of said sheath.

16. The protective cover of claim 15 wherein said sheath is selectively removable from and insertable into said sleeve.

17. The protective cover of claim 15 further comprising at least one shock absorber disposed on said sheath to cushion impact between said sheath and said sleeve.

18. A method of protecting a surgical endoscope head when not in use from damage due to impact comprising the steps of:
 (a) inserting the endoscope head longitudinally into a protective sleeve having open proximal and distal ends and sufficient rigidity to absorb impact without becoming deformed when dropped onto or colliding with a hard surface, the distal end of the inserted endoscope head being proximally spaced from the distal end of the protective sleeve;
 (b) gripping the inserted endoscope head to retain the head in a longitudinally fixed position within said sleeve; and
 (c) permitting free flow of disinfectant liquid within said sleeve along the periphery of said inserted endoscope head.

19. The method of claim 18 wherein step (b) includes resiliently engaging the periphery of said endoscope head only at a single location adjacent the proximal end of said sleeve.

20. A method of protecting a surgical endoscope head from damage due to impact comprising the steps of:
 (a) inserting the endoscope head longitudinally into a protected sleeve having sufficient rigidity to absorb impact without becoming deformed when dropped onto or colliding with a hard surface;
 (b) gripping the inserted endoscope head to retain the head in a longitudinally fixed position within said sleeve; and
 (c) permitting free flow of liquid within said sleeve along the periphery of said inserted endoscope head;
 wherein step (a) includes inserting said endoscope head into a sheath disposed substantially concentrically within said sleeve such that the inserted portion of the endoscope head is spaced from the sheath interior surface, and such that the sheath exterior surface is spaced from the sleeve interior surface.

* * * * *